US006546232B1

(12) United States Patent
Sack et al.

(10) Patent No.: US 6,546,232 B1
(45) Date of Patent: Apr. 8, 2003

(54) MOBILE TELEPHONE WITH A GPS RECEIVER AND EKG ELECTRODES

(75) Inventors: Stefan Sack, Essen (DE); Raimund Erbel, Essen (DE)

(73) Assignee: Vita Phone GmbH, Mannheim (DE)

( * ) Notice: Subject to any disclaimer, the term of this patent is extended or adjusted under 35 U.S.C. 154(b) by 0 days.

(21) Appl. No.: 09/367,846

(22) PCT Filed: Feb. 5, 1998

(86) PCT No.: PCT/EP98/00626

§ 371 (c)(1),
(2), (4) Date: Aug. 26, 1999

(87) PCT Pub. No.: WO98/38611

PCT Pub. Date: Sep. 3, 1998

(30) Foreign Application Priority Data

Feb. 26, 1997 (DE) .......................... 197 07 681

(51) Int. Cl.⁷ .............................. A61B 5/04; H04M 1/72
(52) U.S. Cl. .............................. 455/90; 607/30; 342/57
(58) Field of Search .............................. 455/90; 607/30; 342/57; 379/93

(56) References Cited

U.S. PATENT DOCUMENTS

| | | | | |
|---|---|---|---|---|
| 4,751,726 A | * | 6/1988 | Hepp et al. ................... | 379/93 |
| 5,485,163 A | * | 1/1996 | Singer ......................... | 342/457 |
| 5,544,661 A | * | 8/1996 | Davis et al. ................. | 128/700 |
| 5,862,803 A | * | 1/1999 | Besson et al. .............. | 128/903 |
| 5,941,829 A | * | 8/1999 | Saltzstein et al. ........... | 600/509 |
| 6,083,248 A | * | 7/2000 | Thompson .................... | 607/30 |

FOREIGN PATENT DOCUMENTS

| | | |
|---|---|---|
| DE | 296 00 600 | 6/1996 |
| DE | 196 39 492 | 5/1997 |
| EP | 0 310 379 | 4/1989 |
| EP | 0 679 041 | 10/1995 |
| GB | 2 285 135 | 6/1995 |

* cited by examiner

Primary Examiner—Thanh Cong Le
Assistant Examiner—Alan T. Gantt
(74) Attorney, Agent, or Firm—Nixon Peabody LLP; David S. Safran

(57) ABSTRACT

A mobile telephone with a housing (1), a transmitter, at least one receiver, a call number memory, and keys (2) located on the housing. The keys (2) include at least one emergency key (5) which is rendered prominent in size and/or color relative to the other keys and which when activated causes dialing of an emergency number stored in the call number memory. Furthermore, at least two electrodes, and preferably four electrodes (6, 7, 8, 9) which enable reception of EKG signals are connected to the housing, an EKG signal converter being provided which evaluates the EKG signals, transforms them to a form suitable for transmission, and transmits them to the transmitter.

8 Claims, 1 Drawing Sheet

MOBILE TELEPHONE WITH A GPS RECEIVER AND EKG ELECTRODES

BACKGROUND OF THE INVENTION

Field of the Invention

The invention relates to a mobile telephone with a housing, a transmitter, at least one receiver, a call number memory, and with keys located on the housing.

These generic mobile telephone are currently known in a host of versions. In addition to the aforementioned features, currently mobile telephones generally have a LCD display and an often telescoping antenna which is attached to the housing. The important distinguishing features between the different mobile telephones are on the one hand differences in design, weight and functionality, and on the other hand belonging to one of the existing mobile radiotelephone networks. In addition to the analog C-network, there are also the digital D1, D2 and e-networks. Other mobile radiotelephone networks are moreover being considered. Existing mobile radiotelephone networks differ on the one hand, as already mentioned, by the underlying transmission technique, on the other by the degree of coverage within which telephone calls can be made via these mobile radiotelephone networks. The objective of all networks is for the subscriber to be able to make telephone calls both within the mobile radiotelephone network and also using the land-line telephone networks from anywhere by a correspondingly developed network infrastructure. The existing mobile radiotelephone networks also enable at least in part telephone calls to be set up from remote regions, for example while hiking.

With known mobile telephones it is of course also possible to transmit emergency medical calls from remote areas which are located within the receiving/transmitting area of the pertinent mobile radiotelephone network. Here for example the emergency number can be filed in a call number memory which is present in most mobile phones and can be retrieved by a corresponding key combination on the mobile phone. But here emergency situations can occur in which the owner of the mobile phone himself is no longer able to input the corresponding key combination nor is he able any longer to communicate to a possible companion the corresponding key combination of his special emergency call. This plays a role especially when the holder the of mobile phone suffers from a life-threatening disease and is under the care of a special medical institution which knows the clinical picture of its patient and thus can initiate suitable coordinated assistance measures in an emergency call. These coordinated assistance measures cannot generally be guaranteed via nationwide central emergency numbers.

Especially in patients with cardiovascular disease the described situations occur regularly, viewed in statistical terms. Diseases of the cardiovascular system are at the top of the all pathological processes in Germany. Coronary heart disease is the most frequent cause of death in the industrialized West. In Germany, for example, roughly 300,000 individuals are affected annually by cardiac infarction. In one such cardiac infarction the most frequent complications with generally fatal outcome are arrhythmia and cardiac insufficiency. In Germany, 60,000 individuals suffer sudden cardiac death annually. This cardiac death is characterized by sudden cardiac arrest which generally ends in death without immediate measures of cardiopulmonary resuscitation. Causes of sudden cardiac death are 80 to 90% so-called ventricular flutter or ventricular fibrillation (tachycardiac arrhythmia), 10 to 15% acute myocardial infarction, and 5% brachycardiac arrhythmia. The survival rate of patients suffering sudden cardiac death is between 5 and 20%. It is largely decisive for the level of the survival how quickly suitable assistance measures can be taken.

A host of individuals with a high risk of cardiac infarction are conscious of their risk according to corresponding studies and make every effort to minimize this risk by as much as possible forgoing situations in which immediate assistance measures cannot be taken. Thus, for example, the affected individuals avoid frequenting locations without companions where the probability of being immediately found in case of a cardiac infarction is low, since in these cases they must expect that their survival chances are almost zero if sudden cardiac death occurs.

SUMMARY OF THE INVENTION

Proceeding from the prior art, the object of the invention is to embody and develop known mobile telephones such that they offer a suitable emergency call function for patients with life-threatening health risks.

In accordance with the invention, the aforementioned object is achieved by there being on the housing at least one emergency call key which is rendered prominent in size and/or color and which when activated causes dialing of an emergency number stored in the call number memory. The embodiment of a known mobile telephone in accordance with the invention ensures that in a medical emergency with debilitating physical and mental effects, an emergency call can be transmitted to a competent monitoring center by pressing of the prominent emergency key by the patient himself or by a companion who need not be involved. If the patient remains conscious, he can then communicate his location and complaint to the monitoring center. The patient can then be calmed and monitored via the existing emergency call line; furthermore a history can be taken and specific assistance measures can be initiated.

A first advantageous embodiment of the invention consists in that there is an identification means which causes transmission of data which enable identification when the emergency key is activated. This identification ensures that the monitoring center can initiate specific emergency measures immediately via the patient data stored for example in the EDP system also for the case in which the patient is unconscious. This measure also makes it possible for example to identify a patient when the unconscious patient is found by an uninvolved individual and the emergency call is transmitted by this individual. This identification is possible for example via the call number of the mobile phone which is transmitted on a standard basis in some mobile radiotelephone networks when a connection is set up.

If furthermore there is a release means which causes release of position data when the emergency key is activated, it is ensured that the position of the patient can also be established for the case in which the patient has pressed the emergency key so-to-speak with his last breath. This configuration also makes it possible to find the patient in this situation and to initiate immediate assistance measures. Some mobile radiotelephone networks technically enable this position-finding solely based on the fact that this mobile radiotelephone networks are divided into so-called cells and it can be ascertained from which cell of the mobile radiotelephone network the emergency call was initiated. In this case no special means for position-finding is necessary.

Very accurate position-finding is enabled by there being a position receiver which receives and evaluates external position signals and a position signal converter which transforms the signals of the position receiver to make them suitable for transmission and transmits them to the transmitter. Using this position receiver it is for example possible, based on the signals of the global positioning system (GPS), to accurately determine the position of the patient to within a few meters. These signals are then supplied via the position signal converter to the transmitter which in turn transmits them to the monitoring center so that highly precise data on the position of the patient are available accordingly in the monitoring center.

Another improvement in the initiation of the corresponding immediate assistance measures is guaranteed by the fact that there are at least two, preferably four, electrodes which enable reception of electrocardiogram (EKG) signals and which are connected to the housing and an EKG signal converter which evaluates the EKG signals, transforms them to make then suitable for transmission, and transmits them to the transmitter. In a mobile telephone configured in this way the patient himself or a companion places the electrodes on the bare chest of the patient, whereupon an EKG is derived which is automatically sent to the monitoring center. This configuration enables differential diagnosis of acute cardiac infarction (ST high takeoff) or an underlying arrhythmia (tachycardia, bradycardia) or electrical cardiac arrest (asystole). EKG acquisition and transmission enable estimation of the vital threat to the patient and initiation of the correspondingly suitable emergency measures. Based on the transmitted EKG, resuscitation by a nonprofessional companion or an individual who may be in the vicinity can be influenced and controlled via the mobile phone.

The latter measure is developed especially advantageously by the EKG electrodes being located on the back of the housing facing away from the keys. In this case an EKG is simply recorded by the mobile phone being placed with its back on the bare chest of the patient. An appropriate action is very simple in this case.

Alternatively to the arrangement of the EKG electrodes on the back of the housing, it is advantageous under certain circumstances for the EKG electrodes to be located on a carrier which is connected to the housing via a cable in the removed state and connected directly to the housing in the rest state. In this configuration the application of the carrier to the bare chest of the patient is again optimized based on a preferably correspondingly adapted shape and at the same time it is possible to record an EKG for example also during resuscitation by a nonprofessional, at the same time a companion being in voice communications with the monitoring center to control the nonprofessional resuscitation.

Finally, the mobile phone in accordance with the invention is further advantageously configured in that there is a receiving level sensor which causes output of a warning signal and which detects departure for the receiving/transmitting area of the mobile radiotelephone network. This guarantees that the patient is always notified whether at the instant in fact a connection to the monitoring center is possible in case of an emergency call.

DETAILED DESCRIPTION OF THE INVENTION

Figures 1, 2:
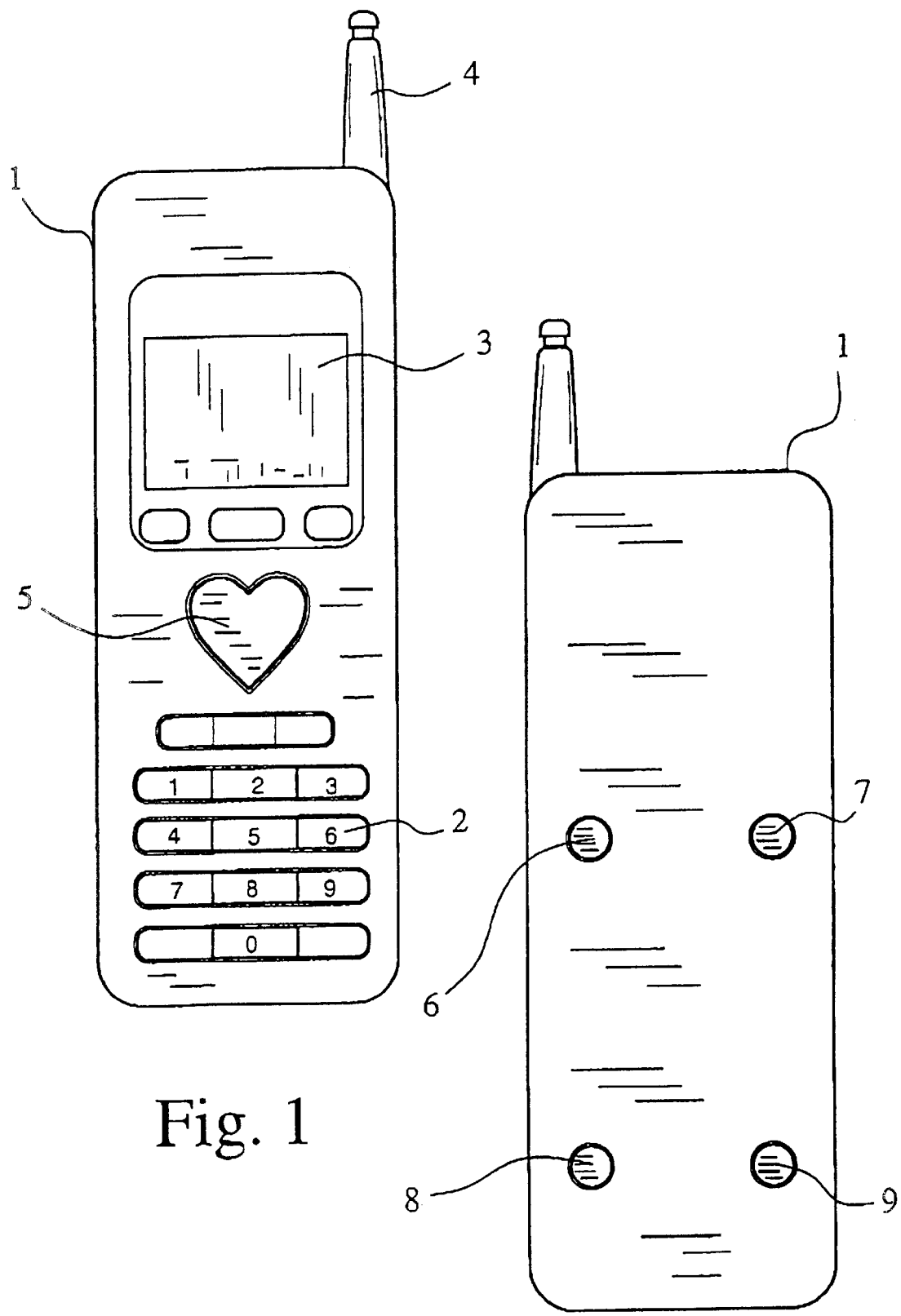
FIG. 1 shows one embodiment of a mobile phone as claimed in the invention in a front view and FIG. 2 shows the embodiment of a mobile phone as claimed in the invention in a back view.

The embodiment of a mobile phone in accordance with in the invention shown in FIG. 1 in a front view has a housing 1, not shown, and located in the housing, a transmitter, at least one receiver and a call number memory, and keys 2 located on the housing 1. In addition, the mobile phone has a LCD display 3 and an antenna 4. In accordance with the invention, on the housing 1 there is on the housing 1 an emergency key which is prominent in size and/or color and which when activated causes dialing of an emergency number stored in the call number memory. In the embodiment shown the emergency key 5 is clearly larger than the conventional keys 2. To further identify its function the emergency key 5 is made heart-shaped and in the embodiment is emphasized by being offset and red.

The identification and release means, position receiver, position signal converter, EKG signal converter and receiving level sensor which are provided according to different embodiments of the mobile phone in accordance with the invention are made as electronic units and are located in the housing, not shown in the drawings.

FIG. 2 finally shows the embodiment of a mobile phone as claimed in the invention in a back view. In the back view it can be clearly seen that on the back of the housing 1 facing away from the keys there are four EKG electrode 6, 7, 8, 9 which with the mobile phone with the back placed on the bare chest of the patient make it possible to derive an EKG.

Other conceivable embodiments of the mobile telephone as claimed in the invention are for example additional lettering of the emergency key 5 for example with the word "emergency call" and/or attachment of fastening, possibilities on the housing 1 which enable the mobile telephone in accordance with the invention to be carried on the chest via a shoulder strap.

What is claimed is:

1. Mobile telephone capable of transmitting EKG signals and permitting voice communication from a remote location to a EKG monitoring center comprising:

a housing, a transmitter, at least one receiver, and a call number memory located within the housing, keys located on a front side of the housing wherein said keys include a set of dialing keys for initiating wireless telephone calls and at least one emergency key which is rendered prominent in at least one of size and color relative to other of said keys and which when activated causes dialing of an emergency number stored in the call number memory, at least two electrodes which enable reception of EKG signals and which are connected to an EKG signal converter in the housing, and an EKG signal converter located within the housing which evaluates the EKG signals, transforms them to a form suitable for transmission, and transmits them to the transmitter;

wherein the EKG electrodes are located in a back side of the housing opposite the front side of the housing facing away from the keys and positioned to enable the back side of the mobile phone to be placed directly on a patient's bare chest in order that the at least two EKG electrodes are able to make contact with the bare chest and can receive EKG signals from the patient while permitting access to the keys on the front side of the housing and voice communication during cardiac monitoring.

2. Mobile telephone as claimed in claim 1, wherein said at least two electrodes comprises four electrodes.

3. Mobile telephone as claimed in claim 1, further comprising an identification means for causing identification data to be transmitted when the emergency key is activated.

4. Mobile telephone as claimed in claim 3, further comprising release means for releasing position data when the emergency key is activated.

5. Mobile telephone as claimed in claim 1, further comprising release means for releasing position data when the emergency key is activated.

6. Mobile telephone as claimed in claim 5, further comprising a position receiver which receives and evaluates external position signals and a position signal converter connected to the position receiver, the position signal converter transforming signals produced by the position receiver into a form suitable for transmission and transmits them to the transmitter.

7. Mobile telephone as claimed in claim 6, further comprising a receiving level sensor for detecting departure of the telephone from a receiving/transmitting area of a mobile radiotelephone network and for causing a warning signal to be output when said departure is detected.

8. Mobile telephone as claimed in claim 1, comprising a receiving level sensor for detecting departure of the telephone from a receiving/transmitting area of a mobile radiotelephone network and for causing a warning signal to be output when said departure is detected.

* * * * *